United States Patent
Imai et al.

(10) Patent No.: US 6,489,533 B2
(45) Date of Patent: Dec. 3, 2002

(54) WATER-DECOMPOSABLE ABSORBENT ARTICLE AND METHOD FOR PRODUCING IT

(75) Inventors: Shigeo Imai, Kagawa (JP); Sachiyo Suzuki, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 66 days.

(21) Appl. No.: 09/760,524

(22) Filed: Jan. 16, 2001

(65) Prior Publication Data

US 2001/0018578 A1 Aug. 30, 2001

(30) Foreign Application Priority Data

Jan. 21, 2000 (JP) ........................................ 2000-012699

(51) Int. Cl.[7] ............................................... A61F 13/15
(52) U.S. Cl. ....................................... 604/364; 604/358
(58) Field of Search ................................ 604/364, 358, 604/265, 287, 288

(56) References Cited

U.S. PATENT DOCUMENTS 5,981,012 A * 11/1999 Pomplun et al. ............ 428/335
5,985,396 A * 11/1999 Kerins et al. ................ 428/335
6,258,427 B1 * 7/2001 Kerins et al. ................ 428/195
6,294,238 B1 * 9/2001 Pomplun et al. ............ 428/335

* cited by examiner

Primary Examiner—John J. Calvert
Assistant Examiner—Angela J Grayson
(74) Attorney, Agent, or Firm—Darby & Darby

(57) ABSTRACT

A water-decomposable absorbent article including an absorbent body that has a water-decomposable top sheet, a water-decomposable back sheet, a water-decomposable adsorbent core sandwiched between the top sheet and the back sheet, and an adhesive layer provided on the back sheet to fit the absorbent article to an external support; and a water-decomposable release sheet for protecting the adhesive layer before use with covering the adhesive layer. The release sheet includes a release layer that faces the adhesive layer, a water-decomposable fibrous layer, and a water-soluble polymer layer sandwiched between the release layer and the fibrous layer. A basis weight of the release layer is at least 0.05 g/m$^2$ but smaller than 0.3 g/m$^2$, and an equilibrium contact angle between a surface of the release layer and a water drop thereon is at least 100 degrees.

5 Claims, 4 Drawing Sheets

WATER-DECOMPOSABLE ABSORBENT ARTICLE AND METHOD FOR PRODUCING IT

BACKGROUND OF THE INVENTION

1. Field of the Invention

The present invention relates to a water-decomposable absorbent article for pantiliners, sanitary napkins, incontinence pads, diapers, etc.

2. Description of the Related Art

Recently, water-decomposable absorbent articles disposable in flush toilets have come available, including, for example, pantiliners, sanitary napkins, incontinence pads, diapers, etc. Such a water-decomposable absorbent article comprises a water-decomposable top sheet to face the skin of a wearer (i.e., the top sheet serves as a body facing surface), a water-decomposable back sheet to face an external support such as an underwear (i.e., the back sheet serves as a garment facing surface), and a water-decomposable absorbent core sandwiched between the top sheet and the back sheet. In general, the back sheet is provided with an adhesive layer via which the absorbent article is fitted to the external support such as an underwear, and the adhesive layer is covered with a release sheet so as not to degrade its adhesiveness until use. Before use, the release sheet is peeled off to expose the adhesive layer outside, and the absorbent article is fitted to the external support via the thus-exposed adhesive layer.

Water-decomposable absorbent articles have self-sustaining strength enough to keep their shape during use, and, after used, they are disposed of in toilets and readily decomposed in water. However, the release sheet which is to be peeled off before use, is made of a resin sheet or a cardboard sheet coated thick with silicone, and is very troublesome since it must be treated as wastes. If the release sheet is also made from a water-decomposable material, it can be disposed of in toilets without requiring treating as wastes, and thereby being convenient to users.

In that situation, Japanese Unexamined Patent Publication (Kokai) No. Heisei 11-47187 discloses a water-decomposable individual packaging absorbent article, for which is used a water-decomposable release sheet. The water-decomposable release sheet used for it is made of a water-soluble resin film or a water-soluble paper coated with a silicone or Teflon for release treatment, and the absorbent article is individually wrapped with the release sheet.

However, the water-soluble resin film coated with a silicone or Teflon for release treatment is problematic in that, when it is stored for a long period of time in high-humidity environments, the film absorbs water and swells, and, as a result, the strength of the wrapping bag of the film is lowered. Another problem with it is that the swollen film will cause surface defects such as pin holes through the release treatment portion of silicone or the like. Such surface defects tend to zip the release sheet when the release sheet is released from the adhesive layer of the absorbent article, and, as a result, smoothly releasing the release sheet from the adhesive layer will be often difficult. In case where the water-soluble resin film is made thick to increase its wet strength, such a thick film will gel in water when disposed of in flush toilets, and will clog drainpipes. The water-soluble paper coated with the lubricant (silicone) is also problematic in that the hydrophobic, three-dimensionally crosslinking release layer of silicone or Teflon will bond fibers of the water-soluble paper to each other, and, as a result, the release sheet will be poorly or hardly decomposable in water.

Japanese Unexamined Patent Publication (Kokai) No. Heisei 8-48950 discloses a release sheet prepared by sizing a water-decomposable paper with a water-soluble sizing agent followed by coating a surface thereof with silicone. However, the invention disclosed in this patent publication is essentially directed to a technique of recycling used paper for regenerated paper, and not to a technique of ensuring rapid decomposition in water of silicone-coated water-decomposable paper and of preventing the surface defects of the coating film of silicone. Japanese Unexamined Patent Publication (Kokai) No. Heisei 6-218006 discloses a water-degradable release liner prepared by coating water-degradable paper with a solution of polyvinylpyrrolidone, drying it, and further coating it with a lubricant silicone layer. In the disclosed release liner, however, the polymer material of polyvinylpyrrolidone is not heat-sealable. Therefore, when the release liner is tried to individually wrap absorbent articles with it, it cannot be formed into bags through heat-sealing via polyvinylpyrrolidone.

In those disclosed in the above-mentioned Japanese Unexamined Patent Publication (Kokai) Nos. Heisei 6-218006 and 8-48950, a water-soluble resin is infiltrated into the fiber-to-fiber space in water-decomposable paper, or water-decomposable paper is coated with a water-soluble resin solution thereby to size the paper. However, the composite film of water-decomposable paper and a water-soluble resin, which is produced by infiltrating the water-soluble resin into water-decomposable paper or by coating water-decomposable paper with the water-soluble resin solution in the manner disclosed, is still problematic in that a surface of the composite film tends to be roughened owing to the roughness of the constituent fibers. In case where a release layer of silicone or the like is formed on such a rough surface of the composite film, it could not have a uniform thickness since the underlying composite film does not have a flat surface. As a result, when the water-soluble resin in the composite film has absorbed water to swell, the release layer that overlies the composite film will have surface defects such as pinholes. Still another problem with the composite film produced by coating water-decomposable paper with the water-soluble resin solution is that the composite film is often warped in the step of drying it after coated with the resin solution, owing to the difference in the wet expansion coefficient between the water-decomposable paper and the water-soluble resin. As a result, when a release layer of crosslinked silicone or the like is formed on such a warped composite film, it will be cracked or will have surface defects such as pin holes.

Through the surface defects (cracks and pin holes) of the release layer, water will penetrate into the underlying water-soluble resin layer to swell or gel it, and the thus-swollen or gelled resin layer will be exposed outside through the surface defects of the release layer. If so, the release properties of the release layer for facilitating easy release of the release sheet from an adhesive layer will be thereby lowered, and, as a result, smoothly peeling the release sheet from the adhesive layer of an absorbent article will be difficult.

SUMMARY OF THE INVENTION

An object of the invention is to provide a water-decomposable absorbent article provided with an adhesive layer to which is fitted a water-decomposable release sheet, wherein the release sheet is improved so that its release layer is flat and is resistant to water, that it is well decomposable in water and that its releasability from the adhesive layer is surely kept for a long period of time.

Another object of the invention is to provide such a water-decomposable absorbent article, in which the release sheet can be formed into a bag for packaging the absorbent article and it can be heat-sealed via a water-soluble polymer layer that underlies the release layer.

According to one aspect of the invention, a water-decomposable absorbent article may comprise: an absorbent body that includes a water-decomposable top sheet, a water-decomposable back sheet, a water-decomposable adsorbent core sandwiched between the top sheet and the back sheet, and an adhesive layer provided on the back sheet to fit the absorbent article to an external support; and a water-decomposable release sheet for protecting the adhesive layer before use with covering the adhesive layer, wherein;

the release sheet includes a release layer that faces the adhesive layer, a water-decomposable fibrous layer, and a water-soluble polymer layer sandwiched between the release layer and the fibrous layer, a basis weight of the release layer is at least 0.05 g/m$^2$ but smaller than 0.3 g/m$^2$, and an equilibrium contact angle between a surface of the release layer and a water drop thereon is at least 100 degrees.

Preferably, the release layer is made from a silicone compound layer, and its weight is at most 0.15 g/m$^2$.

The release sheet for the water-decomposable absorbent article of the invention comprises a release layer of silicone or the like formed on a water-decomposable fibrous layer of, for example, water-decomposable paper or water-decomposable non-woven fabric, via a water-soluble polymer layer therebetween. In this, therefore, the lubricant constituting the release layer does not penetrate into the fiber-to-fiber space in the fibrous layer to bond the constituent fibers, and the decomposability in water of the release sheet is not lowered. When the release sheet is disposed of in flush toilets, water penetrates into the water-soluble polymer layer existing between the fibrous layer and the release layer, to thereby dissolve the polymer layer, and, after all, the release layer is readily peeled off from the thus-dissolved polymer layer in water jets.

In the invention, the weight of the release layer is specifically defined to fall within the range as above, and, in addition, the equilibrium contact angle between the surface of the release layer and a water drop thereon is specifically defined to be at least 100 degrees. Being so defined, the release layer is flat and is resistant to water. Therefore, even when the release sheet is stored under a high-humidity condition for a long period of time or water adheres thereto in the process of producing it, or while its release layer is kept in contact with a water-soluble adhesive, water hardly penetrates into its water-soluble polymer layer via its release layer. As a result, the water-soluble polymer that constitutes the polymer layer is prevented from being swollen or gelled by water, as little water penetrates into the layer, and the release layer is hardly damaged to have surface defects such as pin hole. For these reasons, the release sheet ensures good releasability from the adhesive layer for a long period of time. In addition, the release layer is readily dispersed in water, as the uppermost limit of its weight is defined as set forth above.

Preferably, the thickness of the water-soluble polymer layer falls between 5 $\mu$m and 20 $\mu$m. Also preferably, the water-soluble polymer layer is formed from a polyvinyl alcohol, and the polyvinyl alcohol for the layer has a degree of saponification of at least 70%.

In case where such a water-soluble polymer layer of which the thickness falls within the defined range is formed on the water-decomposable fibrous layer, the influence of the surface roughness of the fibrous layer on the polymer layer can be reduced than conventionally, and the release layer can be well formed on the polymer layer in a more stable condition. In addition, the polymer layer of which the thickness falls within the defined range can reduce the stress to warp the release sheet.

Also preferably, the release sheet is to form a bag to entirely wrap and envelop the absorbent article therein, and its outer periphery is heat-sealed via the polyvinyl alcohol layer to form the bag.

According to another aspect of the invention, the method for producing the water-decomposable absorbent article that includes a water-decomposable top sheet, a water-decomposable back sheet, a water-decomposable absorbent core sandwiched between the top sheet and the back sheet, and an adhesive layer provided on the back sheet to fit the absorbent body to an external support, may comprise;

a step of melt-extruding and laminating a water-soluble polymer layer having a thickness of from 5 $\mu$m to 20 $\mu$m on a surface of a water-decomposable fibrous sheet made of hydrophilic and water-insoluble fibers, a step of applying a release material onto a surface of the water-soluble polymer layer to form thereon a release layer having a weight of at least 0.05 g/m$^2$ but smaller than 0.3 g/m$^2$, a step of crosslinking the release material such that an equilibrium contact angle between the surface of the release layer and a water drop thereon is at least 100 degrees, thereby forming a release sheet, and a step of fitting the release sheet to the adhesive layer of the absorbent body via the release layer.

In the method, the water-soluble polymer layer is melt-extruded and laminated on the fibrous layer. In this, therefore, it is easy to define the thickness of the polymer layer to fall within the desired range.

DESCRIPTION OF THE PREFERRED EMBODIMENTS

Figure 1:
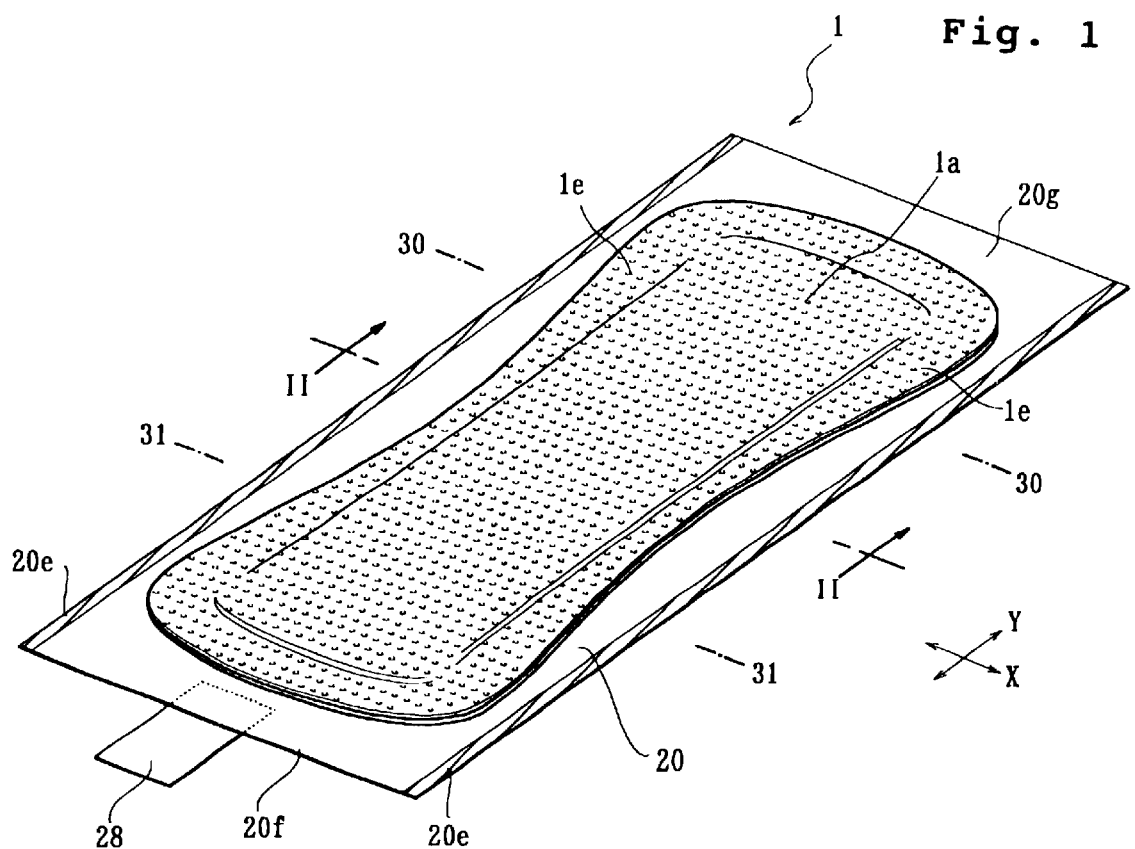
FIG. 1 is a perspective view of one embodiment of an absorbent article of the invention.
Figure 2:
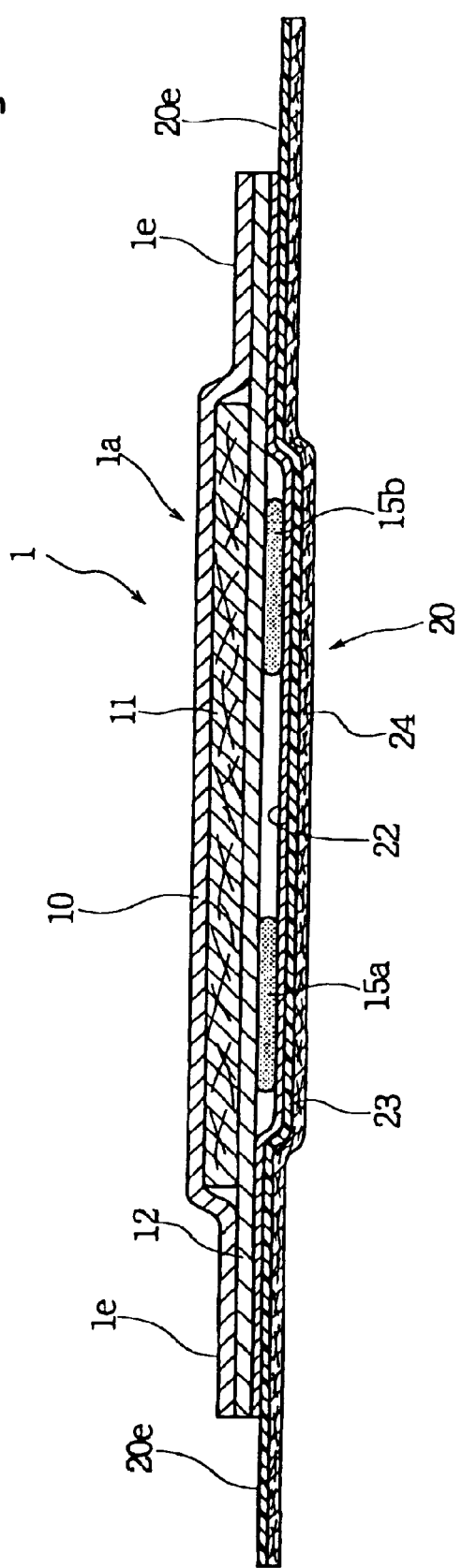
FIG. 2 is a cross-sectional view of the absorbent article of FIG. 1, cut along the line II—II.
Figure 3:
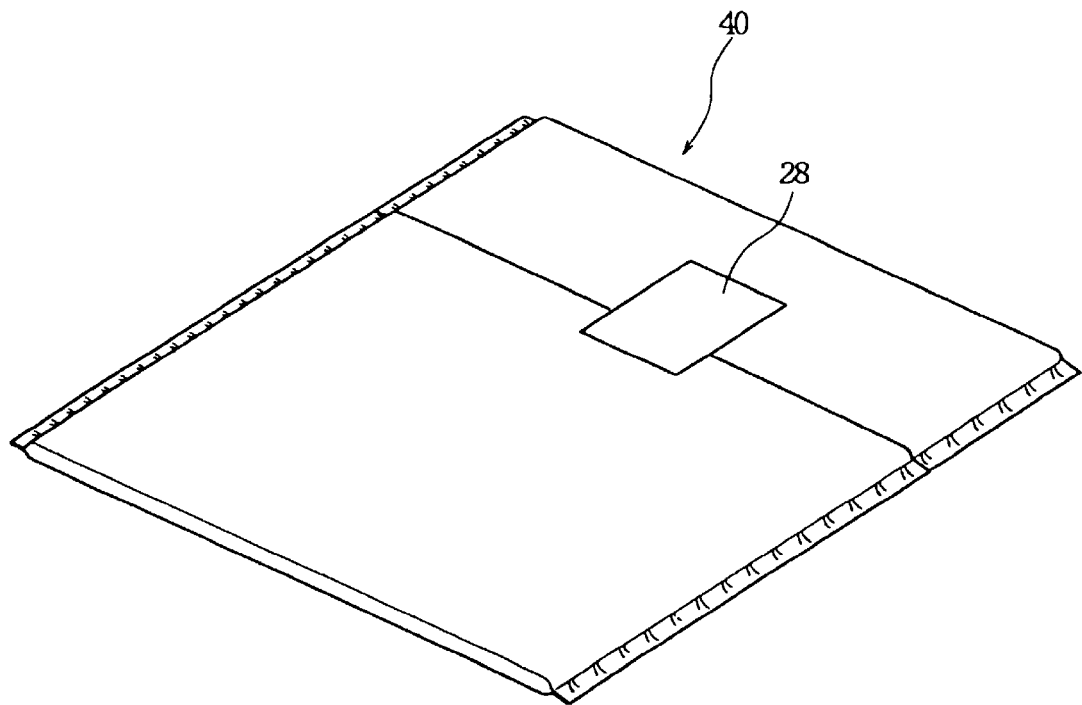
FIG. 3 is a perspective view of the absorbent article of FIG. 1, wrapped and enveloped in a bag of a release sheet.

The invention is described with reference to the accompanying drawings. FIG. 1 is a perspective view of one embodiment of a water-decomposable absorbent article of the invention, seen from its top surface (that shall face the skin of a wearer); FIG. 2 is a cross-sectional view of the absorbent article of FIG. 1, cut along the line II—II; and FIG. 3 is a perspective view of the absorbent article of FIG. 1, wrapped and enveloped in a bag of a release sheet. In these drawings, a longitudinal direction of the illustrated absorbent article is designated by Y, and a transverse direction generally perpendicular to the direction Y is designated by X.

The water-decomposable absorbent article according to the invention shown in FIG. 1 is for pantiliners or sanitary napkins, and this is decomposable in water. As shown in FIG. 2, the absorbent article 1 comprises an absorbent body 1a which includes a water-decomposable and liquid-pervious top sheet 10 that shall face the skin of a wearer, a water-decomposable and liquid-impervious back sheet 12, and a water-decomposable absorbent core 11 sandwiched between the top sheet 10 and the back sheet 12. In an outer peripheral region 1e of the absorbent body 1a, the top sheet 10 and the back sheet 12 are bonded to each other with a water-soluble adhesive or via hydrogen bonding formed by thermally embossing them.

On the outer surface of the back sheet 12, provided is water-soluble adhesive layers 15a, 15b, which is to fit the absorbent body 1a of the absorbent article 1 to an external support such as an underwear while the absorbent article 1 is used. The adhesive layers 15a, 15b extend in the direction Y of the absorbent article 1 in a length of from ½ to 9/10 of the longitudinal dimension of the absorbent article 1. To the adhesive layers 15a, 15b, directly fitted is a release sheet 20 that protects the adhesiveness of the adhesive layers 15a, 15b until use.

The release sheet 20 has a three-layered structure, comprising a release layer 22 (this release layer is also referred to as a lubricant layer) that faces the adhesive layers 15a, 15b; a fibrous layer 24; and a water-soluble polymer layer 23 sandwiched between the release layer 22 and the fibrous layer 24.

The undermost layer, fibrous layer 24 of the release sheet 20 may be made of water-dispersible fibers of pulp, rayon or the like, or may be made of non-woven fabric that is prepared by processing a web of water-dispersible fibers through water-jet treatment or air-through treatment. The water-dispersible fibers for forming the fibrous layer 24 may be combined with any other fibers of polylactic acid, polyethylene, polypropylene, polyacryl or polyester.

Preferably, the fibers constituting the fibrous layer 24 are insoluble in water. If the fibrous layer 24 contains water-soluble fibers, the fibers will absorb water to swell. If so, the water-soluble polymer layer 23 will also swell to be fluid, and will move along with the swollen water-soluble fibers. More preferably, the fibers constituting the fibrous layer 24 are hydrophilic so that the sheet 24 can readily decompose in water after the release sheet 20 has been disposed of in water.

If desired, the fibrous layer 24 may contain a carboxyl group-having synthetic polymer (e.g., carboxymethyl cellulose) or natural substance capable of bonding the constituent fibers through hydrogen bonding therebetween, and may further contain a polysaccharide derivative serving as a binder to enhance the strength of the fibrous layer 24. For example, an alkali metal salt of carboxymethyl cellulose may be added to the fibrous layer 24 in an amount of from 0.1 to 15% by weight of the constituent fibers.

The polymer compound for forming the water-soluble polymer layer 23 on the fibrous layer 24 includes, for example, water-soluble polyvinyl alcohol and polyvinyl alcohol derivatives; polyvinylpyrrolidone; polysaccharide derivatives such as methyl cellulose and starch; polyacrylic acid, polymethacrylic acid, polymaleic acid and their derivatives; polyether compounds such as polyethylene glycol. Among those, preferred are polyvinyl alcohol and its derivatives, as being highly soluble in water and being sealable under heat. Polyvinyl alcohol having a higher degree of saponification is more highly soluble in water. Therefore, it is desirable that polyvinyl alcohol for use herein has a degree of saponification of at least 70%. The hydroxyl groups in polyvinyl alcohol will often form intramolecular or intermolecular hydrogen bonds to lower the solubility in water of the thus hydrogen-bonded polyvinyl alcohol. To solve the problem, therefore, the skeleton chain of polyvinyl alcohol for use herein is preferably grafted or copolymerized with a functional group of highly hydrophilic oxyethylene or oxypropylene. The thus-grafted or copolymerized polyvinyl alcohol is highly soluble even in cold water.

Preferably, a basis weight (Metsuke) of the water-soluble polymer layer 23 falls between 5 $g/m^2$ and 15 $g/m^2$ in order that the polymer constituting the layer 23 does not gel to form blocks (i.e., gel-blocking does not occur) in water and the layer 23 is well decomposable in water. Also preferably, the thickness of the layer 23 falls between 5 $\mu$m and 20 $\mu$m.

The water-soluble polymer layer 23 is laminated on the fibrous layer 24 by melt-extruding a water-soluble polymer through a die on the fibrous sheet 24 to form thereon the polymer film having a predetermined thickness. In the step of lamination through melt extrusion, it is easy to form the water-soluble polymer layer 23 having the desired thickness on the surface of the fibrous layer 24. In the invention, however, the step of forming the polymer layer 23 is not limited thereto. The polymer layer 23 may be formed in any other step, so far as its thickness falls within the desired range. For example, a high-viscosity solution of a water-soluble polymer may be applied onto the fibrous layer 24 to form thereon a laminate film of the polymer.

If, however, the basis weight of the water-soluble polymer layer 23 and the thickness thereof are over the desired range as set forth above, the polymer layer 23 will often gel to form large blocks (i.e., cause gel-blocking) when the release sheet 20 is disposed of in water and when the polymer layer 23 is released from the fibrous layer 24 therein. If so, it will take a lot of time before the polymer layer 23 is dissolved in water. On the other hand, if the basis weight and the thickness of the polymer layer 23 are smaller than the defined range, the influence of the surface roughness of the fibrous layer 24 on the overlying polymer layer 23 will significantly increase. If so, the surface of the release layer 22 overlying the polymer layer 23 is difficult to flatten, and, as a result, the release layer 22 will be damaged to have surface defects and could not be well resistant to water. Concretely, the equilibrium contact angle between the surface of the release layer 22 and a water drop thereon could not be at least 100 degrees. This will be described in detail hereinunder.

In case where the thickness of the water-soluble polymer layer 23 falls within the desired range as above, the release sheet 20 is hardly warped, and, as a result, the release layer 22 is prevented from being cracked and from having pin holes through it.

The release layer 22 that overlies the water-soluble polymer layer 23 may be formed from a fluorine compound or a silicone compound. As being readily formed into the layer 23, preferred is a silicone compound. Preferably, the basis weight of the release layer 22 is at least 0.05 $g/m^2$ but smaller than 0.3 $g/m^2$. With its basis weight being defined to fall within the above range, the release layer 22 can satisfy the requirement that the equilibrium contact angle between the surface of the layer 22 and a water drop thereon is at least 100 degrees. The release layer 22 that satisfies the requirement for the contact angle to a water drop thereon is free from surface defects such as pin holes and has a flat surface. Another advantage of the release layer 22 having a thickness falling within the defined range is that, when the water-soluble polymer layer 23 has dissolved in water and the layer 22 has been thus separated from the fibrous layer 24 therein, the layer 22 can be soon dispersed in water. In order to ensure the contact angle of the layer 22 defined herein and to ensure easy dispersion thereof in water, the basis weight of the layer 22 is more preferably from 0.05 g/m² to 0.15 g/m².

Figure 5:
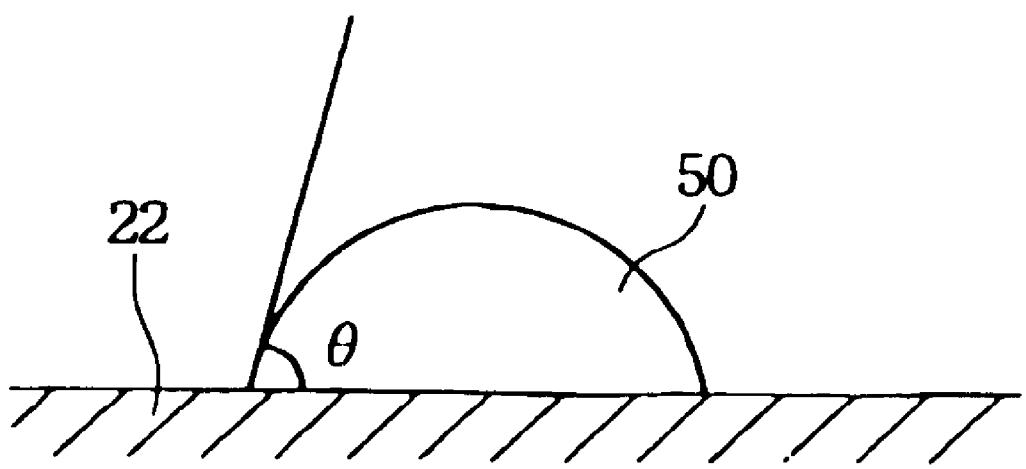
FIG. 5 is an explanatory view indicating a contact angle between the surface of a release layer and a water drop thereon.

The equilibrium contact angle referred to herein is measured with a contact angle meter, "CA-S Micro 2 Model" manufactured by Kyowa Kaimen Kagaku Co., Ltd. Concretely, as shown in FIG. 5, a water drop 50 is put on the surface of the release layer 22, and, after the two have been equilibrated (in 2 minutes after dripping), the contact angle θ between the water drop 50 and the surface of the release layer 22 is measured. The instantaneous contact angle referred to in Table 3 in the following Example is measured in the same manner as set forth above but just after 10 seconds.

If the release layer 22 is damaged to have cracks and pin holes through the surface thereof and the underlying water-soluble polymer layer 23 is exposed out of the release layer 22, the water drop 50 will gradually penetrate into the underlying polymer layer 23, having passed through the surface defects of the layer 22, and will be thereby absorbed by the layer 23. In that case, the contact angle θ will be soon zero (0) without being equilibrated. If such a damaged layer 22 is fitted to the absorbent article 1 after long-term storage of the absorbent article 1, the layer 22 could not be smoothly released from the absorbent body 1a as being zipped by its surface defects.

In case where the silicone compound is used for forming the release layer 22, it may be applied onto the water-soluble polymer layer 23 through gravure coating, flexographic coating or spraying. Among these, preferred is gravure coating, as the amount of the compound to be applied is easy to control and as the compound can form a uniform layer. After the layer 23 has been thus coated or sprayed with it, the silicone compound is then crosslinked thereon so that it is firmly fixed in the interface between the compound layer and the layer 23. For crosslinking it, the silicone compound layer may be heated at a temperature not lower than 100° C. for 1 to 2 minutes, or may be exposed to UV rays (e.g., 350 nm, 120 W/cm) for 1 or 2 seconds or so. In case where polyvinyl alcohol is used to form the water-soluble polymer layer in the invention, the crystallinity thereof will increase under heat and its solubility in water will be thereby greatly lowered. In that case, therefore, the latter crosslinking treatment with the UV rays is preferred.

As shown in FIG. 1, the release sheet 20 formed in the manner as set forth above is rectangular, and has a larger size than the absorbent body 1a. The absorbent body 1a is integrated with the release sheet 20, and then inwardly folded at a position 30—30 as shown in FIG. 1, with the thus-folded absorbent body 1a being inside. Next, this is again inwardly folded a the position 31—31 in the same manner as above. Being thus folded, the opposite side edges 20e, 20e (hatched in FIG. 1) of the release sheet 20 that face to each other are sealed. In this case, the release layer 22 is not formed at least in the area of the opposite side edges 20e, 20e so that the heat-sealable, water-soluble polymer layer 23 of polyvinyl alcohol or the like is exposed outside in that area. With that, the mutually facing release sheets 20 can be heat-sealed or ultrasonically sealed in the area via the water-soluble polymer layer 23 existing therebetween without using an adhesive.

An adhesive tape 28 is provided on one edge 20f of the release sheet 20 as shown in FIG. 1, and this is fitted to an opposite edge 20g thereof as shown in FIG. 3. In that manner, the release sheet 20 forms a bag 40 that envelops the absorbent body 1a therein, with the fibrous layer 24 of the release sheet 20 being outside as shown in FIG. 3. In the illustrated embodiment, the release sheet 20 also serves as a wrapping sheet for the absorbent article to save the resources.

Before use, the adhesive tape 28 is removed from the bag 40 as in FIG. 3, and the absorbent article is unfolded to be placed in its original condition shown in FIG. 1. With that, the release sheet 20 is peeled off from the absorbent body 1a so that the adhesive layers 15a, 15b are exposed outside, and the absorbent body 1a is fitted to the external support such as underwear with the back sheet 12 facing the external support. The unnecessary release sheet 20 (wrapping sheet) is disposed of in flush toilets. In this, the fibrous layer 24 is readily decomposed in water, and water soon penetrates into the water-soluble polymer layer 23 between the fibrous layer 24 and the release layer 22 to dissolve the polymer layer 23, whereby the release layer 22 is readily separated from the polymer layer 23 in water jets and is readily dispersed in water. After used, the absorbent body 1a can also be disposed of in flush toilets, as being decomposable in water.

The top sheet 10 is, for example, made of a water-decomposable non-woven fabric of spun lace. A plurality of sheets of water-decomposable papers may be laminated on a water-decomposable non-woven fabric to form the top sheet 10. In this case, the non-woven fabric and the water-decomposable paper sheets may be integrated through hydrogen bonding or needling. Since the top sheet 10 acts to lead excretions to the underlying absorbent core 11, it is preferably perforated to have a plurality of perforations throughout the entire area thereof as shown in FIG. 1, for example.

The absorbent core 11 may be made of water-decomposable paper, pulp or non-woven fabric. For example, air-laid pulp or the like may be formed into the absorbent core 11, having a basis weight of from 50 to 70 g/m² or so. In case where the absorbent core 11 is made of water-decomposable paper, a plurality of sheets of relatively thin, water-decomposable papers may be stacked to form it. This type of the absorbent core 11 is favorable, as being well decomposable in water. For example, about 4 to 8 sheets of water-decomposable papers having a basis weight of from 10 to 20 g/m² are stacked to form the absorbent core 11. As the case may be, sheets of water-decomposable papers coated with a water-swellable resin such as polyvinyl alcohol or the like may be stacked to form the absorbent core 11.

The back sheet 12 is readily dispersed in water jets in flush toilets or in water in septic tanks, and it may be formed of water-decomposable paper, water-decomposable non-woven fabric or the like that contains water-dispersible fibers. For example, it may be made of (1) a water-decomposable paper sheet of pulp fibers where the pulp fibers are bonded to each other via hydrogen bonding therebetween, (2) a water-decomposable paper sheet of pulp fibers and other water-dispersible fibers of rayon or the like where the constituent fibers are bonded to each other with a water-soluble binder, (3) a water-decomposable paper sheet of water-dispersible fibers where the constituent fibers are simply entangled, or (4) a water-decomposable non-woven fabric of water-dispersible fibers having a relatively short length where the constituent fibers are forcedly entangled through water-jetting treatment. Preferably, the outer surface of the back sheet 12 (this shall face the external support) or the inner surface thereof (this shall face the absorbent core 11) may be coated with a water-soluble resin such as a polyvinyl alcohol, an unsaturated carboxylic acid copolymer or the like. Thus coated, the back sheet 12 will be impervious to fluid.

Figure 4:
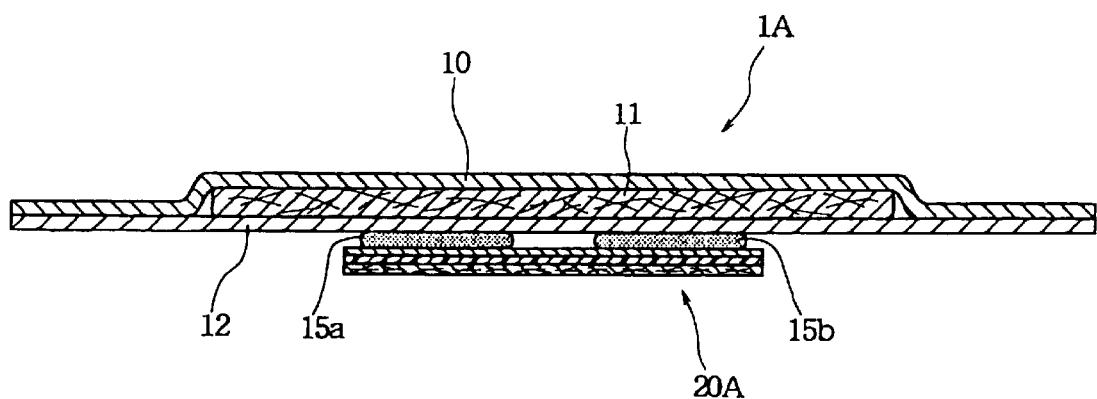
FIG. 4 is a cross-sectional view of another embodiment of the absorbent article of the invention.

FIG. 4 is a cross-sectional view of another embodiment of the absorbent article of the invention. In the absorbent article 1A of FIG. 4, the release sheet 20A only covers the adhesive layers 15a, 15b. In this embodiment, an additional wrapping sheet is required to wrap the absorbent article 1A. As a wrapping sheet, for example, a water-decomposable fibrous layer, a water-soluble resin or a sheet not decomposable in water may be used.

EXAMPLES

The invention is described in more detail with reference to the following Examples, which, however, are not intended to restrict the scope of the invention.

Example 1

A release sheet 20 as shown in FIG. 1 and FIG. 2 was produced to demonstrate one embodiment of the invention. For the fibrous layer 24, used was water-decomposable paper of pulp and rayon. For the water-soluble polymer layer 23, used was polyvinyl alcohol. This was melt-extruded and laminated on the fibrous layer 24. For the release layer 22, used was a silicone compound. This was applied onto the water-soluble polymer layer 23 by gravure-coating, and crosslinked and fixed thereon through exposure to UV rays. The release sheet thus produced was tested for decomposition in water of the fibrous layer and the water-soluble polymer layer. The test result is given in Table 1. Comparative samples were also tested in the same manner as herein. Decomposition in Water:

The samples were tested according to the water-decomposability test in JIS P-4501. Precisely, each sample was cut to have a length of 10 cm and a width of 10 cm, put into a 300 ml beaker filled with 300 ml of ion-exchanged water, and stirred therein with a stirrer. The revolution of the stirrer was 600 rpm. While stirred, the sample was periodically checked, and the time taken by it until its dispersion-in water was recorded.

TABLE 1

|  | Comp. Ex. 1 | Comp. Ex. 2 | Comp. Ex. 3 | Comp. Ex. 4 | Example 1-1 |
|---|---|---|---|---|---|
| Basis weight of release layer (g/m$^2$) | — | — | — | 0.2 | 0.2 |
| Thickness of water-soluble polymer layer (μm) | — | 40 | 20 | — | 20 |
| Basis weight of fibrous web layer (g/m$^2$) | 40 | — | 20 | 40 | 20 |
| Time taken until decomposition in water of fibrous web layer (sec) | 12 | — | 23 | not decomposed in water | 29 |
| Time taken until decomposition in water of water-soluble polymer layer (sec) | — | 138 | 40 | not decomposed in water | 180 |

Example 2

Release sheets were produced in the same manner as in Example 1. In these, however, the thickness of the water-soluble layer 23 as well as the basis weight of the fibrous layer 24 are different. In the test for decomposition in water of each sample, the area of the non-decomposed polymer layer 23, if any, was measured.

TABLE 2

|  | Example 2-1 | Example 2-2 | Example 2-3 | Comp. Ex. 2-1 | Comp. Ex. 2-2 |
|---|---|---|---|---|---|
| Basis weight of release layer (g/m$^2$) | 0.2 | 0.2 | 0.2 | 0.2 | 0.2 |
| Thickness of water-soluble polymer layer (μm) | 15 | 20 | 20 | 30 | 30 |
| Basis weight of fibrous web layer (g/m$^2$) | 20 | 20 | 15 | 20 | 15 |
| Time taken until decomposition in water of fibrous web layer (sec) | 25 | 29 | 22 | 38 | 28 |
| Area of non-decomposed polymer layer (cm$^2$) | 1 | 2 | 2 | 4 | 4 |
| Time taken until decomposition in water of water-soluble polymer layer (sec) | 120 | 180 | 150 | 720 | 480 |

Example 3

Release sheets were produced in the same manner as in Example 1. In these, however, the basis weight of the release layer 22 differs individually. A water drop was put onto the release layer 22 of each sample, and the contact angle, θ, between the surface of the layer 22 and the water drop was measured with the contact angle meter, "CA-S Micro 2 Model" manufactured by Kyowa Kaimen Kagaku Co., Ltd., as shown in FIG. 5. The instantaneous contact angle ref erred to herein is the angle θ measured after 10 seconds; and the equilibrium contact angle also referred to herein is the angle θ measured after 2 minutes.

With its release layer 22 being kept in contact with the adhesive layers 15a, 15b of the absorbent article, the samples were left at 40° C. and 90% RH (relative humidity) for one week and then conditioned at 20° C. and 60% RH for 2 hours. The time-dependent peeling strength of each sample from the absorbent article was measured according to JIS Z0237. In this test, each sample was checked as to whether it was zipped or not when it was released from the absorbent article. For the adhesive layers 15a, 15b, used was an acrylic resin adhesive.

TABLE 3

|  | Example 3-1 | Example 3-2 | Example 3-3 | Example 3-4 | Comp. Example |
|---|---|---|---|---|---|
| Basis weight of release layer (g/m$^2$) | 0.3 | 0.2 | 0.15 | 0.1 | 0.05 |
| Thickness of water-soluble polymer layer (μm) | 15 | 15 | 15 | 15 | 15 |
| Basis weight of fibrous web layer (g/m$^2$) | 20 | 20 | 20 | 20 | 20 |

TABLE 3-continued

| | Example 3-1 | Example 3-2 | Example 3-3 | Example 3-4 | Comp. Example |
|---|---|---|---|---|---|
| Time taken until decomposition in water of fibrous web layer (sec) | 42 | 25 | 21 | 17 | — |
| Area of non-decomposed polymer layer (cm²) | 6 | 1 | 1 | — | |
| Time taken until decomposition in water of water-soluble polymer layer (sec) | 240 | 120 | 40 | 17 | — |
| Initial peeling strength (mN/inch) | 55.1 | 54.90 | 56.3 | 180.4 | 332.4 |
| Zipping | no | no | no | no | yes, a little |
| Peeling strength after one week (mN/inch) | 65.6 | 87.2 | 112.8 | 216.7 | 560.9 |
| Zipping (after one week) | no | no | no | no | yes |
| Instantaneous contact angle (degrees) | | | 107.5 | 107.7 | 102.9 |
| Equilibrium contact angle (degrees) | | | 107 | 106.5 | 0 |

From the test results as above, it is understood that the release sheet of the invention is, even after stored long, not zipped and can well protect the adhesive layer of absorbent articles for a long period of time. In Example 3, the release sheet was able to be heat-sealed Therefore, this type of the release sheet can be used for individually wrapping the absorbent article, and can be heat-sealed in a simplified manner to provide individually wrapped absorbent articles.

As described in detail hereinabove, the release sheet for water-decomposable absorbent articles of the invention is decomposable in water. Therefore, it can be disposed of in toilets without requiring treating as wastes, and is therefore convenient to users. Having the advantage of good decomposability in water, another advantage of the release sheet is that it is resistant to water and is therefore hardly damaged to have surface defects such as cracks and pin holes. Cracks and pin holes, even if formed in the release sheet, do not enlarge. Even after stored for a long period of time, the release sheet well has its releasability from the adhesive layer of absorbent articles.

The absorbent article of the invention may be individually wrapped with the release sheet fitted thereto. Thus wrapped, the absorbent article is convenient to users, since the unnecessary part for use may be reduced and the wrapping sheet can be disposed of in toilets. Specifically, in case where the water-soluble polymer layer of the release sheet is made from a thermoplastic resin, this type of the release sheet can be heat-sealed for individual wrapping, thereby facilitating production of the absorbent articles.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. A water-decomposable absorbent article comprising: an absorbent body that includes a water-decomposable top sheet, a water-decomposable back sheet, a water-decomposable adsorbent core sandwiched between the top sheet and the back sheet, and an adhesive layer provided on the back sheet to fit the absorbent article to an external support; and a water-decomposable release sheet for protecting the adhesive layer before use with covering the adhesive layer, wherein;

the release sheet includes a release layer that faces the adhesive layer, a water-decomposable fibrous layer, and a water-soluble polymer layer sandwiched between the release layer and the fibrous layer, a basis weight of the release layer is at least 0.05 g/m² but smaller than 0.3 g/m², and an equilibrium contact angle between a surface of the release layer and a water drop thereon is at least 100 degrees.

2. The water-decomposable absorbent article as set forth in claim 1, wherein the release layer is formed from a silicone compound, and a basis weight thereof is at most 0.15 g/m².

3. The water-decomposable absorbent article as set forth in claim 1, wherein a thickness of the water-soluble polymer layer falls between 5 μm and 20 μm.

4. The water-decomposable absorbent article as set forth in claim 1, wherein the water-soluble polymer layer is formed from a polyvinyl alcohol, and the polyvinyl alcohol has a degree of saponification of at least 70%.

5. The water-decomposable absorbent article as set forth in claim 4, wherein the release sheet is to be a wrapping sheet for entirely wrapping and enveloping the absorbent article, and has opposite side edges which are heat-sealed via the polyvinyl alcohol.

* * * * *